(12) United States Patent
Pennington et al.

(10) Patent No.: US 9,801,355 B2
(45) Date of Patent: *Oct. 31, 2017

(54) PESTICIDAL CONTROL DEVICE WITH HIGH LOAD OF ACTIVE INGREDIENT

(71) Applicant: BAYER INTELLECTUAL PROPERTY GMBH, Monheim (DE)

(72) Inventors: Robert G. Pennington, Rayville, MO (US); John Rose, Blue Springs, MO (US); Jochem Rueter, Shawnee, KS (US)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/824,145

(22) Filed: Aug. 12, 2015

(65) Prior Publication Data

US 2015/0373947 A1  Dec. 31, 2015

Related U.S. Application Data

(63) Continuation of application No. 13/147,088, filed as application No. PCT/EP2010/000264 on Jan. 19, 2010, now Pat. No. 9,137,989.

(60) Provisional application No. 61/148,233, filed on Jan. 29, 2009.

(51) Int. Cl.
| | |
|---|---|
| *A01K 13/00* | (2006.01) |
| *A01N 25/34* | (2006.01) |
| *A01K 11/00* | (2006.01) |
| *A01N 53/00* | (2006.01) |
| *A01N 57/16* | (2006.01) |
| *B29B 7/82* | (2006.01) |
| *B29C 45/00* | (2006.01) |
| *B29K 27/06* | (2006.01) |
| *B29K 105/12* | (2006.01) |
| *B29K 311/14* | (2006.01) |
| *B29L 31/00* | (2006.01) |

(52) U.S. Cl.
CPC .......... *A01K 13/003* (2013.01); *A01K 11/001* (2013.01); *A01N 25/34* (2013.01); *A01N 53/00* (2013.01); *A01N 57/16* (2013.01); *B29B 7/82* (2013.01); *B29C 45/0001* (2013.01); *B29C 45/0005* (2013.01); *B29K 2027/06* (2013.01); *B29K 2105/12* (2013.01); *B29K 2311/14* (2013.01); *B29K 2995/0037* (2013.01); *B29L 2031/70* (2013.01)

(58) Field of Classification Search
CPC .... A01K 13/003; A01K 11/001; A01N 25/34; A01N 53/00; A01N 57/16; B29B 7/82; B29C 45/0001; B29C 45/0005; B29K 2027/06; B29K 2105/12; B29K 2311/14; B29K 2995/0037; B29L 2031/70
See application file for complete search history.

(56) References Cited

U.S. PATENT DOCUMENTS

| | | | |
|---|---|---|---|
| 4,195,075 A | 3/1980 | Miller | |
| 4,439,415 A | 3/1984 | Hennart et al. | |
| 4,536,368 A | 8/1985 | Hung et al. | |
| 4,536,388 A | 8/1985 | Pearce, III | |
| 4,543,247 A | 9/1985 | von Bittera et al. | |
| 4,544,547 A | 10/1985 | von Bittera et al. | |
| 4,631,231 A | 12/1986 | Stendel et al. | |
| 4,674,445 A * | 6/1987 | Cannelongo | A01K 11/00 119/651 |
| 4,721,064 A | 1/1988 | Denk et al. | |
| 4,879,117 A * | 11/1989 | Rombi | A01K 27/007 424/411 |
| 4,885,855 A | 12/1989 | Marks, Sr. et al. | |
| 4,930,451 A | 6/1990 | Miller et al. | |
| 5,044,114 A | 9/1991 | Haberer | |
| 5,104,659 A | 4/1992 | Fishbein et al. | |
| 5,194,265 A | 3/1993 | Boettcher et al. | |
| 5,266,324 A | 11/1993 | Stendel et al. | |
| 5,271,179 A | 12/1993 | Cohen | |
| 5,294,445 A * | 3/1994 | Sieveking | A01N 25/34 424/405 |
| 5,342,619 A | 8/1994 | Krzewki et al. | |
| 5,472,955 A | 12/1995 | Kellerby | |

(Continued)

FOREIGN PATENT DOCUMENTS

| | | |
|---|---|---|
| CA | 2017139 A1 | 12/1990 |
| FR | 2171941 A1 | 9/1973 |

(Continued)

OTHER PUBLICATIONS

"Cellulosic fiber reinforcement for industrial applications", <http://www.centralfiber.com/pdf/Fiber%20Brochure%20-%20English.pdf>.

International Search Report, PCT/EP2010/000264, dated Apr. 20, 2010, 4 pages.

*Primary Examiner* — Sean Basquill

(74) *Attorney, Agent, or Firm* — McBee Moore Woodward & Vanik IP, LLC

(57) ABSTRACT

The present invention relates to a pesticidal control device that includes at least one pesticidal active ingredient, cellulose fibers, and a polymer or polymer matrix. The combination of the cellulose fibers with the polymer allows for a higher loading of liquid pesticidal active ingredients within the pesticidal control device, maintains the active ingredient within the control device during transportation, storage and handling, and provides higher efficacy or control of pests during treatment. The pesticidal control device may be an ear tag, collar, or bee strip.

20 Claims, 7 Drawing Sheets

(56) References Cited

U.S. PATENT DOCUMENTS

| | | | |
|---|---|---|---|
| 5,620,696 | A | 4/1997 | Krzewki et al. |
| 5,665,822 | A * | 9/1997 | Bitler .................. C05G 3/0029 525/100 |
| 5,776,481 | A | 7/1998 | Karst et al. |
| 5,780,369 | A * | 7/1998 | Allison .................... B32B 5/26 28/104 |
| 5,911,196 | A | 6/1999 | Simmons et al. |
| 6,232,328 | B1 | 5/2001 | Dorn et al. |
| 6,372,242 | B1 | 4/2002 | Gutierrez |
| 6,372,765 | B1 | 4/2002 | Sirinyan et al. |
| 6,668,483 | B1 | 12/2003 | Trivisani et al. |
| 6,896,891 | B2 | 5/2005 | Dorn et al. |
| 7,084,138 | B2 | 8/2006 | Fischer et al. |
| 7,399,817 | B2 | 7/2008 | Wilson, Jr. et al. |
| 9,137,989 | B2 * | 9/2015 | Pennington ............ A01N 25/34 |
| 2002/0195063 | A1 | 12/2002 | Hedde |
| 2004/0202690 | A1 | 10/2004 | Arther et al. |
| 2007/0048343 | A1 | 3/2007 | Merrill et al. |
| 2008/0306095 | A1 | 12/2008 | Crawford |

FOREIGN PATENT DOCUMENTS

| | | |
|---|---|---|
| JP | 2001000092 | 1/2001 |
| WO | 2006127407 A1 | 11/2006 |

* cited by examiner

PESTICIDAL CONTROL DEVICE WITH HIGH LOAD OF ACTIVE INGREDIENT

REFERENCE TO RELATED APPLICATIONS

This application is a continuation of U.S. application Ser. No. 13/147,088, filed Aug. 24, 2011, which is a U.S. national stage application of International Patent Application No. PCT/EP2010/000264, filed Jan. 19, 2010, and claims the benefit of U.S. provisional application No. 61/148,233, filed Jan. 29, 2009, the entire disclosures of which are incorporated herein by reference.

The present invention relates to a pesticidal control device for animals and a method of making the pesticidal control device.

Livestock, particularly cattle, are frequently troubled by pests such as horn flies, face flies, Gulf Coast ticks, spinose ear ticks, and other pests, which can cause not only irritation to the animal and interfere with its normal feeding and grazing habits but also oftentimes infection and illness.

Various methods have been employed to protect animals against these pests. One method has been to spray the hair coats of the livestock with an insecticidal and/or acaricidal solution. Generally, this type of treatment provides protection against the pests for a period of about three weeks. After that time, the treatment is usually ineffective because the insecticidal and/or acaricidal solution is degraded by light, moisture, and microorganisms. In addition, the use of relatively large amounts of the insecticidal and/or acaricidal solution is necessitated by the need to spray the entire surface of the animal and to compensate for the gradual deterioration of the insecticidal and/or acaricidal solution following application to the animal.

Another method has been to use insecticidal and/or acaricidal ear tags. The ear tags release an active ingredient, which spreads when the animal causes the tag to rub its own hair coat or the hair coat of other animals. The active ingredient within the ear tag is slowly released from the tag matrix over a prolonged period and deposited on the hair coat of the livestock. In contrast to the 2-3 week intervals between insecticide spraying, insecticide ear tags can be expected to be effective for at least 3 months.

Currently, the most common material for formulating insecticidal ear tags is polyvinyl chloride. Since polyvinyl chloride must be plasticized to perform satisfactorily as a tag, the quantity of insecticide active ingredient which can be incorporated into the product is reduced in direct proportion to the quantity of plasticizer required. Such high loading of plasticizer and insecticide cause the ear tag to "bleed" (exude) insecticide. This in turn necessitates special packaging to extend shelf life, requires avoiding high temperatures in transport and storage, and demands special handling requirements when the product is removed from the package for application to the animal. The same problems occur with other pesticidal control devices, such as collars or bee strips.

As such, there is a need for a pesticidal control device that can incorporate a higher level of the pesticidal active ingredient without bleeding or the requirement for special packaging, transportation, storage, or handling.

The present invention is directed to a pesticidal control device. The pesticidal control device includes a pesticidal active ingredient, a polymer, and a cellulose fiber. The pesticidal control device may be an ear tag, collar, or bee strip.

The pesticidal control device of the present invention includes at least one insecticidal and/or acaricidal active ingredient, cellulose fibers and a polymer or polymer matrix. The combination of the cellulose fibers with the polymer or polymer matrix specifically allows for a higher level of liquid insecticidal and/or acaricidal active ingredient to be included within the control device of the present invention. In addition, the combination allows the insecticidal and/or acaricidal active ingredient to stay within the control device during transportation, storage, and handling and not bleed. As such, the higher insecticidal and/or acaricidal active ingredient loading of the present invention provides higher efficacy or control of pests during treatment than the typical polymer control devices without cellulose fibers. The addition of fibers to, and the higher levels of liquid insecticidal and/or acaricidal active ingredient included within the control device, necessitates a reduction in the quantity of polymer or polymer matrix in the control devices, compared to, for example, previous ear tags. Such reduction typically reduces the devices' structural integrity, resulting in breakage, premature loss of pesticidal efficacy, and/or the devices' failure to perform. The incorporation of cellulose fibers into the polymer or polymer matrix, however, contribute to maintaining the structural integrity of the control devices. The control devices of the present invention include ear tags, collars, and bee strips. In one embodiment, the control device is an ear tag.

I. PESTICIDAL ACTIVE INGREDIENTS

Figure 1:
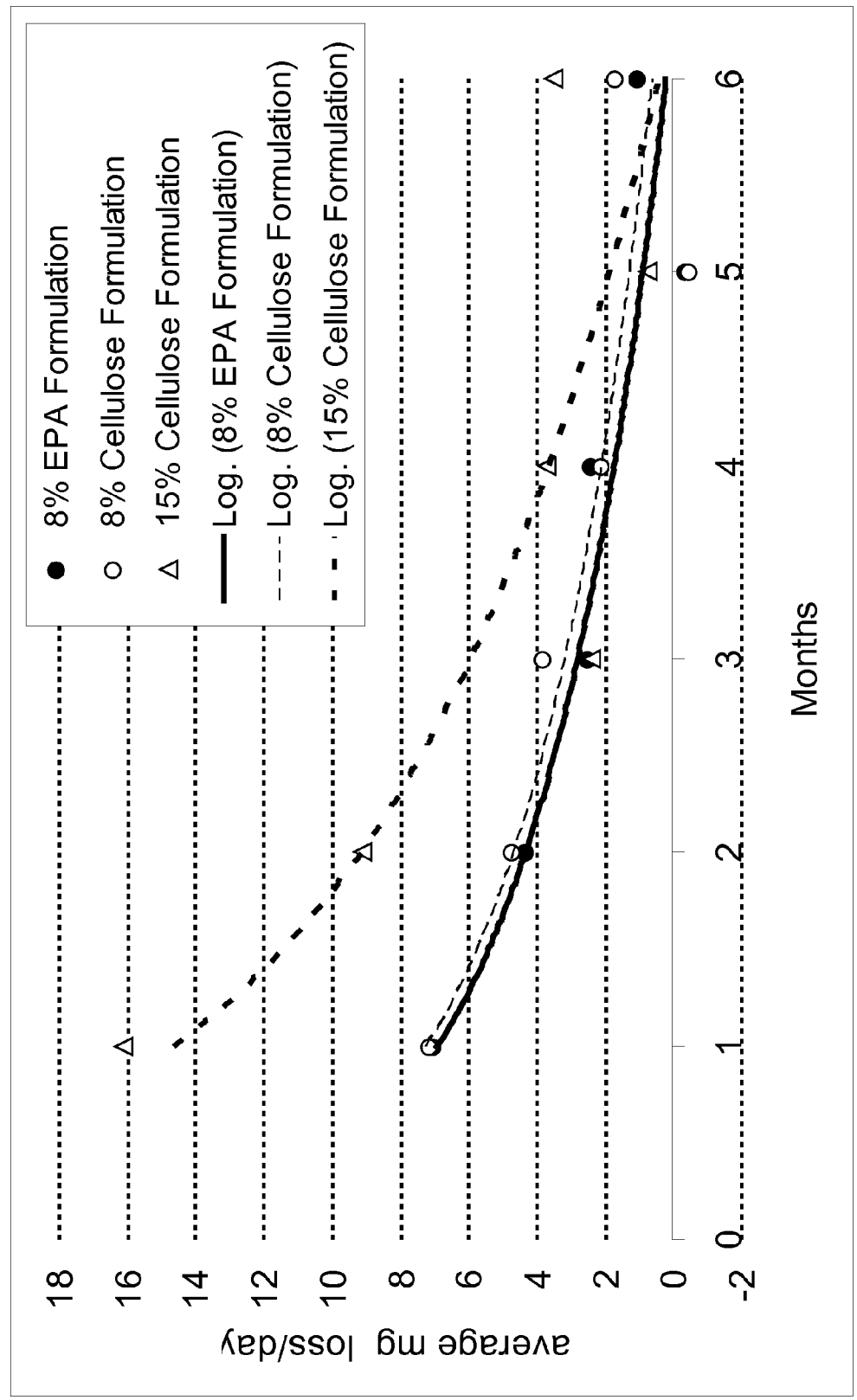
FIG. 1 provides results of active ingredient loss for ear tags tested as described in Example 11.

Various pesticidal active ingredients, insecticides and acaricides, both liquids and solids, can be included in the pesticidal control device of the present invention. The combination of the cellulose fibers and polymer or polymer matrix, however, allows for the inclusion of a higher loading of liquid pesticidal active ingredients, or solids that have been dissolved in a solvent, into the control device than achieved with the polymer or polymer matrix alone. In particular, this embodiment prevents premature bleeding.

In one embodiment, the pesticidal control device includes an insecticidal and/or acaricidal active ingredient selected from the group consisting of an organophosphate, pyrethroid, carbamate, nicotinoid, organochlorine, pyrrole, pyrazole, oxadiazine, macrocyclic lactone, and combinations thereof. In another embodiment of the invention, the pesticidal control device includes two or more insecticidal and/or acaricidal active ingredients. In an exemplary embodiment, the ear tag may include two or more organophosphates.

Suitable organophosphates include 0-ethyl-0-(8-quinolyl) phenyl thiophosphate (quintiofos), 0,0-diethyl 0-(3-chloro4methyl-7-coumarinyl)-thiophosphate (coumaphos), 0,0-diethyl 0-phenylglycoxylonitrile oxime thiophosphate (phoxim), 0,0-diethyl 0-cyanochlorobenzaldoxime thiophosphate (chlorphoxim), 0,0-diethyl 0-(4-bromo-2,5-dichlorophenyl)phosphorothionate (bromophos-ethyl), 0,0,0'0',-tetraethyl S,S'-methylene-di(phosphorodithionate) (ethion), 2,3-p-dioxanedithiol S,S-bis(0,0-diethyl phosphorodithionate), 2-chloro-1-(2,4-dichlorophenyl)-vinyl diethyl phosphate (chlorfenvinphos), 0,0-dimethyl 0-(3-methylthiophenyl)thionophosphate (fenthion), O,O-diethyl O-2-isopropyl-6-methylpyrimidin-4-yl phosphorothioate (diazinon); S-1,2-bis(ethoxycarbonyl)ethyl O,O-dimethyl phosphorodithioate (malathion); and O,O-dimethyl O-4-nitro-m-tolyl phosphorothioate (Sumithion).

Suitable pyrethroids include 3-[2-(4-chlorophenyl)-2-chlorovinyl]-2,2-dimethyl-cyclo-propanecarboxylic acid (α-cyano4fluoro-3-phenoxy)-benzyl ester (flumethrin), α-cyano(4-fluoro-3-phenoxy)-benzyl 2,2-dimethyl-3-(2,2-dichlorovinyl)-cyclopropanecarboxylate (cyfluthrin) an its enantiomers and stereomers, α-cyano-3-phenoxybenzyl(±)-cis,trans-3-(2,2-dichlorovinyl)-2,2-dimethylcyclopropanecarboxylate (deltamethrin), α-cyano-3-phenoxybenzyl 2,2-dimethyl-3-(2,2-dichlorovinyl)cyclopropanecarboxylate (cypermethrin), 3-phenoxybenzyl(±)-cis,trans-3-(2,2-dichlorovinyl)-2,2-dimethylcyclopropanecarboxylate (permethrin), α-cyano-3-phenoxy-benzyl α-(p-Cl-phenyl)isovalrate (fenvalerate), 2-cyano-3-phenoxybenzyl 2-(2-chloro-α,α,α-trifluoro-p-toluidino)-3-methylbutyrate (fluvalinate). Other suitable pyrethroids include [1α,3α(Z)]-(±)-cyano-(3-phenoxyphenyl)methyl 3-(2-chloro-3,3,3-trifluoro-1-propenyl)-2,2-dimethylcyclopropanecarboxylate (cyhalothrine); [1α(S*),3α(Z)]-(±)-cyano-(3-phenoxyphenyl)methyl 3-(2-chloro-3,3,3-trifluoro-1-propenyl)-2,2-dimethylcyclopropanecarboxylate (lambda-cyhalotrin); cyano (3-phenoxyphenyl)methyl-2,2-dimethyl-3-(2-methyl-1-propenyl)-cyclopropanecarboxylate (cyphenothrin); (RS)-cyano-(3-phenoxyphenyl)methyl(S)-4-(difluoromethoxy)-α-(1-methylethyl)benzeneacetate (flucythrinate); cyano(3-phenoxyphenyl)methyl 2,2-dimethyl-3-(1,2,2,2-tetrabromoethyl)cyclopropanecarboxylate (tralomethrin); and [1α,3α(Z)]-(±)-(2-methyl[1,1'-biphenyl]-3-yl)methyl 3-(2-chloro-3,3,3-trifluoro-1-propenyl)-2,2-dimethylcyclopropanecarboxylate (bifenthrin).

The pyrethroid insecticides useful in the present invention include cyano(3-phenoxyphenyl)methyl 4-chloro-α-(1-methylethyl)benzeneacetate (fenvalerate), and the active isomer thereof commonly known as esfenvalerate; cyano(3-phenoxyphenyl)methyl 3-(2,2-dichloroethenyl)-2,2-dimethylcyclopropanecarboxylate (cypermethrin); (3-phenoxyphenyl)methyl 3-(2,2-dichloroethenyl)-2,2-dimethylcyclopropanecarboxylate (permethrin); (3-phenoxyphenyl)methyl 2,2-dimethyl-3-(2-methyl-1-propenyl)cyclopropanecarboxylate (phenothrine); cyano(4-fluoro-3-phenoxyphenyl)methyl 3-(2,2-dichloroethenyl)-2,2-dimethylcyclopropanecarboxylate (cyfluthrin); beta-cyfluthrin (an enriched isomer of cyfluthrin); [1α,3α(Z)]-(±)-cyano-(3-phenoxyphenyl)methyl 3-(2-chloro-3,3,3-trifluoro-1-propenyl)-2,2-dimethylcyclopropanecarboxylate (cyhalothrine); [1α(S*),3α(Z)]-(±)-cyano-(3-phenoxyphenyl)methyl 3-(2-chloro-3,3,3-trifluoro-1-propenyl)-2,2-dimethylcyclopropanecarboxylate (lambda-cyhalotrin); cyano (3-phenoxyphenyl)methyl-2,2-dimethyl-3-(2-methyl-1-propenyl)cyclopropanecarboxylate (cyphenothrin); (RS)-cyano-(3-phenoxyphenyl)methyl(S)-4-(difluoromethoxy)-α-(1-methylethyl)benzeneacetate (flucythrinate); cyano(3-phenoxyphenyl)methyl 2,2-dimethyl-3-(1,2,2,2-tetrabromoethyl)cyclopropanecarboxylate (tralomethrin); and [1α,3α(Z)]-(±)-(2-methyl[1,1'-biphenyl]-3-yl)methyl 3-(2-chloro-3,3,3-trifluoro-1-propenyl)-2,2-dimethylcyclopropanecarboxylate (bifenthrin). To the extent that the active insecticides may exist as optical or geometric isomers, all isomers and racemic mixtures are understood to be included herein. All possible other isomeric forms of the compounds are also included herein.

Suitable carbamates include 2-isopropoxyphenyl N-methylcarbamate (propoxur), (2,2-Dimethyl-1,3-benzodioxol-4-yl) N-methylcarbamate (bendiocarb), crotenon, carbaryl, 3-tolyl N-methylcarbamate, 3,4-xylyl-N-methylcarbamate, m-(1-methylbutyl)-phenyl N-methylcarbamate, 2-ethylthiomethyl-phenyl N-methylcarbamate, 4-dimethylamino-m-tolyl N-methylcarbamate, 2,3-dihydro-2,2-dimethylbenzofuran-7-yl N-methylcarbamate, 2-dimethylcarbamoyl-3-methyl-5-pyrazolyl-dimethylcarbamate, and 2-dimethylamino-5,6-dimethylpyrimidin-4-yl N,N-dimethylcarbamate.

Suitable nicotinoids are preferably chloronicotinyls, such as imidacloprid, thiacloprid, clothianidin, thiamethoxam, acetamiprid, nitenpyram and dinotefuran.

Suitable pyrroles include 4-Bromo-2-(4-chlorophenyl)-1-ethoxymethyl-5-trifluoromethyl-1H-pyrrole-3-carbonitrile (chlorfenapyr).

Suitable pyrazoles include 3-Bromo-N-[4-chloro-2-methyl-6-(methylcarbamoyl)phenyl]-1-(3-chloro-2-pyridine-2-yl)-1H-pyrazole-5-carboxamide(chlorantraniliprole), 3-bromo-1-(3-chloro-2-pyridyl)-4'-cyano-2'-methyl-6'-(methylcarbamoyl)pyrazole-5-carboxanilide (cyantraniliprole), dimethylcarbamoyl-5-methylpyrazol-3-yldimethylcarbamate(dimetilan), 4-chloro-N-[[4-(1,1-dimethylethyl)phenyl]]methyl]-3-ethyl-1-methyl-1H-pyrazole-5-carboxamide(tebunfenpyrad), 4-chloro-3-ethyl-1-methyl-N-[4-(p-tolyloxy)benzyl]pyrazole-5-carboxamide (tolfenpyrad), 5-amino-1-(2,6-dichloro-α,α,α-trifluoro-p-tolyl)-4-ethylsulfinylpyrazole-3-carbonitrile(ethiprole), 1-(2,6-dichloro-α,α,α-trifluoro-p-tolyl)-4-(difluoromethylthio)-5-[(2-pyridylmethyl)amino]pyrazole-3-carbonitrile (pyriprole), and (E)-1-(2,6-dichloro-α,α,α-trifluoro-p-tolyl)-5-(4-hydroxy-3-methoxybenzylideneamino)-4-trifluoromethylthiopyrazole-3-carbonitrile(vaniliprole).

Suitable oxadiazines include (S)-methyl 7-chloro-2,5-dihydro-2-[[(methoxycarbonyl) [4-(trifluoromethoxy)phenyl] amino]carbonyl]indeno[1,2-e][1,3,4]oxadiazine-4a(3H)-carboxylate indoxacarb).

In one embodiment, the ear tag of the present invention includes diazinon and coumaphos. In a further embodiment, the ear tag of the present invention includes beta-cyfluthrin.

In the pesticidal control device of the present invention, the insecticidal and/or acaricidal active ingredients are generally present in an amount of from about 10% to about 70% of the total weight of the control device. In one embodiment, the pesticidal ear tag of the present invention includes from about 15% to about 60% by weight insecticidal and/or acaricidal active ingredient of the total weight of the ear tag. In another embodiment, the pesticidal ear tag of the present invention includes from about 40% to about 60% by weight insecticidal and/or acaricidal active ingredient of the total weight of the ear tag. In yet another embodiment, the pesticidal ear tag of the present invention includes 50% to about 65% by weight insecticidal and/or acaricidal active ingredient of the total weight of the ear tag. In another embodiment, the pesticidal ear tag of the present invention includes from about 40% to about 60% by weight of a mixture of diazinon and coumaphos of the total weight of the ear tag. In yet another embodiment, the ear tag of the present invention includes from about 40% to about 50% by weight of diazinon and from about 5% to about 15% by weight coumaphos of the total weight of the ear tag. In a further embodiment, the ear tag of the present invention includes from about 10% to about 20% by weight beta-cyfluthrin of the total weight of the ear tag.

II. POLYMER

The pesticidal control device of the present invention includes a polymer. Suitable polymers include polyvinyl chloride, polyolefin, polyurethane, polyamide, methacrylate, and silicon polymers. Other suitable polymers include other polyvinyl halides (for instance polyvinyl fluoride); polyacrylate and polymethacrylate esters (for instance polymethyl acrylate and polymethyl acrylate and polymethyl methacrylate); and polymers of vinyl benzenes (for instance, polystyrene and polymer polymerized vinyl toluene). In one embodiment, the polymer is a polyvinyl chloride. In another embodiment, the polymer of the present invention is a polyurethane.

In one embodiment, the pesticidal ear tag of the present invention includes from about 20% to about 60% by weight polymer of the total weight of the ear tag. In another embodiment, the pesticidal ear tag of the present invention includes from about 35% to about 45% by weight polymer of the total weight of the ear tag.

III. CELLULOSE FIBERS

The pesticidal control device of the present invention also includes cellulosic fibers. Cellulosic fibrous materials suitable for use in the present invention include softwood fibers and hardwood fibers. Exemplary, though not exclusive, types of softwood pulps are derived from slash pine, jack pine, radiata pine, loblolly pine, white spruce, lodgepole pine, redwood, and douglas fir. North American southern softwoods and northern softwoods may be used, as well as softwoods from other regions of the world. Hardwood fibers may be obtained from oaks, genus *Quercus*, maples, genus *Acer*, poplars, genus *Populus*, or other commonly pulped species. In general, softwood fibers are preferred due to their longer fiber length as measured by T 233 cm-95, and southern softwood fibers are most preferred due to a higher coarseness as measured by T 234 cm-84, which leads to greater intrinsic fiber strength as measured by breaking load relative to either northern softwood or hardwood fibers.

The fibrous material may be prepared from its natural state by any pulping process including chemical, mechanical, thermomechanical (TMP) and chemithermomechanical pulping (CTMP). These industrial processes are described in detail in R. G. Macdonald & J. N. Franklin, Pulp and Paper Manufacture in 3 volumes; 2.sup.nd Edition, Volume 1: The pulping of wood, 1969, Volume 2: Control, secondary fiber, structural board, coating, 1969, Volume 3: Papermaking and paperboard making, 1970, The joint Textbook Committee of the Paper Industry, and in M. J. Kocurek & C. F. B. Stevens, Pulp and Paper Manufacture, Vol. 1:Properties of Fibrous Raw Materials and Their Preparation for Pulping, The joint Textbook Committee of the Paper Industry, 1983, 182 pp. Preferably, the fibrous material is prepared by a chemical pulping process, such as a Kraft or sulfite process. In particular the Kraft process is especially preferred. Pulp prepared from a southern softwood by a Kraft process is often called SSK. In a similar manner, southern hardwood, northern softwood and northern hardwood pulps are designated SHK, NSK & NHK, respectively. Bleached pulp, which is fibers that have been delignified to very low levels of lignin, are preferred, although unbleached Kraft fibers may be preferred for some applications due to lower cost, especially if alkaline stability is not an issue. Desirably, the chemically treated cellulose fiber has been derived from a source which is one or more of Southern Softwood Kraft, Northern Softwood Kraft, hardwood, eucalyptus, mechanical, recycle and rayon, preferably Southern Softwood Kraft, Northern Softwood Kraft, or a mixture thereof, more preferably, Southern Softwood Kraft. One example of a cellulose fiber is Cellulose Reinforcing Fiber, commercially available from Central Fiber (Wellsville, Kans.).

In one embodiment, the pesticidal control device of the present invention includes from about 2% to about 20% by weight cellulose fibers of the total weight of the control device. In another embodiment, the pesticidal ear tag of the present invention includes from about 5% to about 15% by weight cellulose fibers of the total weight of the ear tag. In yet another embodiment, the pesticidal ear tag of the present invention includes from about 5% to about 12% by weight cellulose fibers of the total weight of the ear tag.

IV. OTHER ADDITIVES

The pesticidal control device of the present invention generally includes a plasticizer. Suitable plasticizers include phthalates (i.e., diethyl phthalate, dioctyl phthalate, diphenyl phthalate, dicyclohexyl phthalate, dimethyl phthalate, dioctyl phthalate, and dihexyl phthalate); sebacates (i.e., dipentyl sebacate, n-butyl benzyl sebacate and dibenzyl sebacate); adipates (i.e., isobutyl adipate, dioctyl adipate, diisobutyl adipate and dinonyl adipate); citrates (i.e., acetyltributyl citrate and acetyl triethyl citrate), and trimellitates. Other suitable plasticizers include, for example, hydrogenated polyphenols; alkylated aromatic hydrocarbons; polyester plasticizers, for example polyesters of polyols, such as hexanediol, polycarboxylic acids, such as sebacic or adipic acid, having molecular weights of about 2000, and epoxide plasticizers such as epoxidized soybean oil, epoxidized linseed oil and epoxidized tall oils (such as octyl epoxy tallate). One example of commercially available epoxidized soybean oil is Drapex® 6.8, commercially available from Chemtura (Middlebury, Conn.). Additional suitable plasticizers include esters of azelaic acid, maleic acid, ricinolic acid, myristic acid, palmitic acid, oleic acid, stearic acid and trimellitic acid. In one embodiment, the pesticidal ear tag of the present invention includes from about 1% to about 50% by weight plasticizer of the total weight of the ear tag. In another embodiment, the pesticidal ear tag of the present invention includes from about 10% to about 40% by weight plasticizer of the total weight of the ear tag. In yet another embodiment, the pesticidal ear tag of the present invention includes from about 20% to about 30% by weight plasticizer of the total weight of the ear tag.

Other additives such as dyes, pigments, lubricants, fillers, thickners and stabilizers may be included in the control device. Suitable stabilizers include anti-oxidants, ultraviolet stabilizers, and polymer stabilizers. In one embodiment, the stabilizer is a calcium-zinc type polyvinyl chloride stabilizer. One example of a commercially available calcium-zinc type polyvinyl chloride stabilizer is Mark® 1034, commercially available from Chemtura (Middlebury, Conn.). Suitable thickners include silicon dioxide commercially available, for example, as Cab-O-Sil® from Cabot Corporation (Tuscola, Ill.). If these materials are included, they are generally present in an amount of from about 1% to about 10% by weight of the total weight of the pesticidal control device. In another embodiment, these materials are included in an amount of from about 2% to about 5% by weight of the total weight of the pesticidal ear tag.

In one embodiment, the pesticidal control device of the present invention also includes an insecticidal and/or acaricidal synergist. The synergist potentiates the activity of the insecticidal and/or acaricidal active ingredient. Suitable synergists include piperonyl butoxide, N-octylbicycloheptenedicarboximide, triphenyl phosphate, S-421 (bis(2,3,3,3-tetrachloropropyl) ether), MGK-264 (N-(2-ethylhexyl)bicyclo[2.2.1]hept-5-ene-2,3-dicarboximide), IBTA (isobornyl thiocyanatoacetate) and N-(2-ethylhexyl)-1-isopropyl-4-methylbicyclo[2.2.2]oct-5-ene-2,3-dicarboximide.

V. PESTICIDAL CONTROL DEVICE

Generally to prepare the pesticidal control device of the present invention a polymer, cellulose fibers, an insecticidal and/or acaricidal active ingredient, plasticizer, and a stabilizer are mixed together. The mixture is then molded into a control device. The control device is selected from the group consisting of ear tags, collars, and bee strips. Techniques for molding the ear tags, collars, and bee strips of the present invention are known to those skilled in the art. Molding includes either injection or extrusion. One molding method for ear tags is disclosed in U.S. Pat. No. 4,195,075. Other techniques may include casting, laminating, and die-cutting.

In one embodiment, the cellulose fibers and polymer are heated to allow the polymer to expand and better absorb the active ingredient. The active ingredient is either in liquid form or is dissolved with a solvent prior to addition to the cellulose fibers and polymer mixture. Once the active ingredient is added the product is cooled to contract the polymer. This product is then mixed with the plasticizer, stabilizer, other active, and/or other ingredients and then molded.

Techniques for attaching the molded insect control device to an animal, such as livestock, are also well known in the art. As used herein, the term "livestock" is intended to include cattle, sheep, pigs, horses, and other animals.

The following examples are simply intended to further illustrate and explain the present invention. The invention, therefore, should not be limited to any of the details in these examples.

EXAMPLES

Example 1—Cellulose/Virgin PVC Matrix

Formula A

| Ingredients | % w/w | grams |
|---|---|---|
| 1. Diazinon (87%) | 46.0 | 345.0 g |
| 2. Coumaphos | 10.4 | 78.0 g |
| 3. Mark ® 1034 | 0.29 | 2.2 g |
| 4. Drapex ® 6.8 | 2.1 | 15.8 g |
| 5. PVC | 29.21 | 219.0 g |
| 6. Cellulose Fibers | 12.0 | 90.0 g |
| | 100.0% | 750.0 g |

Mixed Ingredients 3, 4, 5, and 6 in a Marion mixer with Paddle blender and heated to 170° F. Added ingredient 1 and heated at 170° F. for 3 hours. Cooled to 70° F. and added ingredient 2 and mixed for 1 hour. Injection molded using Trubor 50 ton/3.5 oz injection molder.

Put 5 tags in clay coated laminated foil pouches at ambient temperature and 5 tags unpackaged at ambient temperature and 1 tag in a glass jar at 50° C. After 72 hours in 50° C. oven, tag was very wet (diazinon pooled at the bottom of the jar). After sitting at ambient temperature, the packaged and unpackaged tags looked good (dry).

Example 2—PVC Matrix

Formula B

| Ingredients | % w/w | grams |
|---|---|---|
| 1. Diazinon (87%) | 46.0 | 345.0 g |
| 2. Coumaphos | 10.4 | 78.0 g |
| 3. Mark ® 1034 | 0.4 | 3.0 g |
| 4. Drapex ® 6.8 | 3.0 | 22.5 g |
| 5. PVC | 40.2 | 301.5 g |
| | 100.0% | 750.0 g |

Mixed Ingredients 3, 4, and 5 in a Marion mixer with Paddle blender and heated to 170° F. Added ingredient 1 and heated at 170° F. for 3 hours. Cooled to 70° F. and added ingredient 2 and mix for 1 hour. Injection molded using Trubor 50 ton/3.5 oz injection molder.

The premix was extremely wet and runny even after adding coumaphos, and was therefore not moldable into an ear tag.

Example 3—Diazinon/Coumaphos Ear Tag

| % w/w | Ingredients |
|---|---|
| 40.71 | 1. Diazinon (85.98%) |
| 15.66 | 2. Coumaphos (95.8%) |
| 12.00 | 3. Cellulose Fibers |
| 30.53 | 4. SuperKleen 2223BF-95 (PVC/plasticizer blend, purchased from AlphaGary Co., Leominster, MA) |
| 0.10 | 5. D&C Green #6 (Color) |
| 1.00 | 6. Titanium Dioxide |
| 100.0 | |

Mixed Ingredients 3, 4, and 5 in a Marion mixer with Paddle blender and heated to 170° F. Added ingredient 1 and heated at 170° F. for 3 hours. Cooled to 70° F. and added ingredient 2 and 6 and mixed for 1 hour. Injection molded using Trubor 50 ton/3.5 oz injection molder.

Example 4—Diazinon/Coumaphos Ear Tag

| % w/w | Ingredients |
|---|---|
| 40.71 | 1. Diazinon (85.98%) |
| 15.66 | 2. Coumaphos (95.8%) |
| 27.85 | 3. PVC |
| 0.28 | 4. Mark ® 1034 |
| 2.50 | 5. Drapex ® 6.8 |
| 12.00 | 6. Cellulose Fibers |
| 1.00 | 7. Titanium Dioxide |
| 100.0 | |

Mixed Ingredients 3, 4, 5 and 6 in a Marion mixer with Paddle blender and heated to 170° F. Added ingredient 1 and heated at 170° F. for 3 hours. Cooled to 70° F. and added ingredient 2 and 7 and mixed for 1 hour. Injection molded using Trubor 50 ton/3.5 oz injection molder.

Example 5—Beta-cyfluthrin Ear Tag

| % w/w | Ingredients |
|---|---|
| 15.08 | 1. Beta-cyfluthrin (99.5%) |
| 34.92 | 2. Diethyl Phthalate |
| 7.00 | 3. Cellulose Fibers |
| 41.94 | 4. SuperKleen 2223BF-95 (PVC/plasticizer blend, purchased from AlphaGary Co., Leominster, MA) |
| 0.06 | 5. D&C Red #17 (Color) |
| 1.00 | 6. Titanium Dioxide |
| 100.0 | |

Heated ingredient 2 to 150° F. and add ingredient 1, mixed until ingredient 1 is melted (liquid premix). In a Marion mixer with paddle blender added ingredients 3 and 4 and heated to 170° F. Added liquid premix to Marion mixer and heated to 170° F. for 3 hours. Cooled to 100° F. and added ingredients 5 and 6 and mixed for 30 minutes. Injection molded into cattle ear tags using Trubor 50 ton/3.5 oz injection molder.

Example 6—Beta-cyfluthrin Ear Tag

| % w/w | Ingredients |
|---|---|
| 15.08 | Beta-cyfluthrin (99.5%) |
| 34.92 | Diethyl Phthalate |
| 7.00 | Cellulose Fibers |
| 37.40 | PVC |
| 0.37 | Mark® 1034 |
| 3.73 | Drapex® 6.8 |
| 0.50 | FD&C Yellow #6 (Color) |
| 1.00 | Titanium Dioxide |
| 100.0 | |

Heated ingredient 2 to 150° F. and added ingredient 1, mixed until ingredient 1 is melted (liquid premix). In a Marion mixer with paddle blender added ingredients 3, 4, 5, and 6 and heated to 170° F. Added liquid premix to Marion mixer and heated to 170° F. for 3 hours. Cooled to 100° F. and added ingredients 7 and 8 and mix for 30 minutes. Injection molded into cattle ear tags using Trubor 50 ton/3.5 oz injection molder.

Example 7

Two ear tags prepared as described in Example 5 were observed for 3 months, one at ambient temperature and one at 50° C., to determine the storage stability of the ear tag, i.e. the % active remaining in the ear tag, and to see its visual appearance, i.e. was it wet or dry.

Percent active remaining in the ear tag is calculated by dissolving the tag in suitable solvent, extracting the remaining active and analyzing with GCP.

| Analyses | Target | Limits | Method |
|---|---|---|---|
| Appearance | dry | | visual (pass/fail) |
| Beta-cyfluthrin | 15.0% w/w | 14.25-15.75% w/w | |

| Assay Time Interval | Appearance | % beta-cyfluthrin |
|---|---|---|
| Ambient Temperature | | |
| 0 month | Pass | 15.05% |
| 1 month | Pass | 14.33% |
| 2 month | Pass | 14.81% |
| 3 month | Pass | 14.67% |
| 50° C. | | |
| 0 month | Pass | 15.05% |
| 1 month | Pass | 14.44% |
| 2 month | Pass | 14.80% |
| 3 month | Pass | 14.56% |

Example 8

Two ear tags prepared as described in Example 6 were observed for 3 months, one at ambient temperature and one at 50° C., to determine the storage stability of the ear tag, i.e. the % active remaining in the ear tag, and to see its visual appearance, i.e. was it wet or dry.

Percent active remaining in the ear tag is calculated by dissolving the tag in suitable solvent, extracting the remaining active and analyzing with GCP.

| Analyses | Target | Limits | Method |
|---|---|---|---|
| Appearance | dry | | visual (pass/fail) |
| Beta-cyfluthrin | 15.0% w/w | 14.25-15.75% w/w | |

| Assay Time Interval | Appearance | % beta-cyfluthrin |
|---|---|---|
| Ambient Temperature | | |
| 0 month | Pass | 14.75% |
| 1 month | Pass | 13.86% |
| 2 month | Pass | 14.25% |
| 3 month | Pass | 14.20% |
| 50° C. | | |
| 0 month | Pass | 14.75% |
| 1 month | Pass | 14.86% |
| 2 month | Pass | 14.80% |
| 3 month | Very slight oil on outside of tag | 14.66% |

Example 9

Two ear tags prepared as described in Example 3 were observed for 3 months, one at ambient temperature and one at 50° C., to determine the storage stability of the ear tag, i.e. the % active remaining in the ear tag, and to see its visual appearance, i.e. was it wet or dry.

Percent active remaining in the ear tag is calculated by dissolving the tag in suitable solvent, extracting the remaining active and analyzing with GCP.

| Analyses | Target | Limits | Method |
|---|---|---|---|
| Appearance | dry | | visual (pass/fail) |
| Coumaphos | 15.0% w/w | 14.25-15.75% w/w | |
| Diazinon | 35.0% | 33.95-36.05% w/w | |

| Assay Time Interval | Appearance | % diazinon | % coumaphos |
|---|---|---|---|

-continued

| | Ambient Temperature | | |
|---|---|---|---|
| 0 month | Pass | 34.99% | 14.50% |
| 1 month | Pass | 34.91% | 14.63% |
| 2 month | Pass | 35.32% | 14.30% |
| 3 month | Pass- completely dry - no oil coming out of tag | 35.95% | 16.08%* |

| | 50° C. | | |
|---|---|---|---|
| 0 month | Pass | 34.99% | 14.50% |
| 1 month | Pass | 35.04% | 14.89% |
| 2 month | Pass | 34.91% | 14.40% |
| 3 month | Slightly oily residue leaching out on to surface | 35.86% | 15.99%* |

*high out of limits

Example 10

Two ear tags prepared as described in Example 4 were observed for 3 months, one at ambient temperature and one at 50° C., to determine the storage stability of the ear tag, i.e. the % active remaining on the ear tag, and to see its visual appearance, i.e. was it wet or dry.

Percent active remaining in the ear tag is calculated by dissolving the tag in suitable solvent, extracting the remaining active and analyzing with GCP.

| Analyses | Target | Limits | Method |
|---|---|---|---|
| Appearance | dry | | visual (pass/fail) |
| Coumaphos | 15.0% w/w | 14.25-15.75% w/w | |
| Diazinon | 35.0% | 33.95-36.05% w/w | |

| Assay Time Interval | Appearance | % diazinon | % coumaphos |
|---|---|---|---|
| | Ambient Temperature | | |
| 0 month | Pass | 34.67% | 14.60% |
| 1 month | Pass | 34.28% | 14.27% |
| 3 month | Pass | 35.86% | 15.62% |
| The 2nd month assay was inadvertently missed. | | | |
| | 50° C. | | |
| 0 month | Pass | 34.67% | 14.60% |
| 1 month | Pass | 35.84% | 14.84% |
| 3 month | Slightly oily residue leaching out on to surface | 34.98% | 15.82% |

The 2$^{nd}$ month assay was inadvertently missed.

Example 11

The following formulations were applied to the ears of cattle on pasture. Four sample tags from each formulation were collected at monthly intervals for six consecutive months. The sample tags were weighed and duplicate assays conducted on each tag to quantify the mean amount of active ingredient remaining in the tags at each monthly interval. The mean amounts of the active ingredients remaining in the collected tags at each monthly interval were subtracted from the mean amounts of active ingredients found in the tags assayed at the prior monthly data point to determine the amount and rate of active ingredient depletion over the six month study duration.

Formula 1—8.0% beta-cyfluthrin/20% Piperonyl Butoxide—EPA Formulation (Control)

| Ingredient | % w/w |
|---|---|
| Beta-cyfluthrin (99.5%) | 8.04 |
| Piperonyl butoxide | 20.00 |
| Titanium Dioxide | 1.00 |
| FD&C Violet #2 (Color) | 0.03 |
| SuperKleen 2223 BF-70 | 70.93 |
| (PVC/plasticizer blend, purchased from AlphaGary Co., Leominster, MA) | 100.0 |

Formula 2—8.0% beta-cyfluthrin/20% Piperonyl Butoxide Cellulose Formulation

| Ingredient | % w/w |
|---|---|
| Beta-cyfluthrin (99.5%) | 8.04 |
| Piperonyl butoxide | 20.00 |
| Titanium Dioxide | 1.00 |
| Cellulose (regenerated fibers) | 7.00 |
| SuperKleen 2223 BF-70 | 63.96 |
| (PVC/plasticizer blend, purchased from AlphaGary Co., Leominster, MA) | 100.0 |

Formula 3—15.0% beta-cyfluthrin Cellulose Formulation

| Ingredient | % w/w |
|---|---|
| Beta-cyfluthrin (99.5%) | 15.08 |
| Diethyl phthalate | 22.50 |
| Titanium Dioxide | 1.00 |
| Cellulose (regenerated fibers) | 7.00 |
| FD&C Red #17 | 0.03 |
| SuperKleen 2223 BF-70 | 54.39 |
| (PVC/plasticizer blend, purchased from AlphaGary Co., Leominster, MA) | 100.0 |

Number of Test Animals per Treatment

| Formula | Treatment | No. of animals |
|---|---|---|
| 1 | 8% beta-cyfluthrin/ 20% Piperonyl Butoxide EPA | 14 |
| 2 | 8% beta-cyfluthrin/ 20% Piperonyl Butoxide Cellulose | 14 |
| 3 | 15% beta-cyfluthrin Cellulose | 14 |

Each animal received two tags of the same formula and a record was kept showing which animal received which test substance tag in which ear. All animals were treated (tagged with the test substance ear tags) on the same day. Four tags representative of each test substance were collected from treated animals at monthly intervals (±6 days) for six consecutive months post treatment. Extra, unused tags remaining at the six month collection date were removed from the treated animals.

Figure 2:
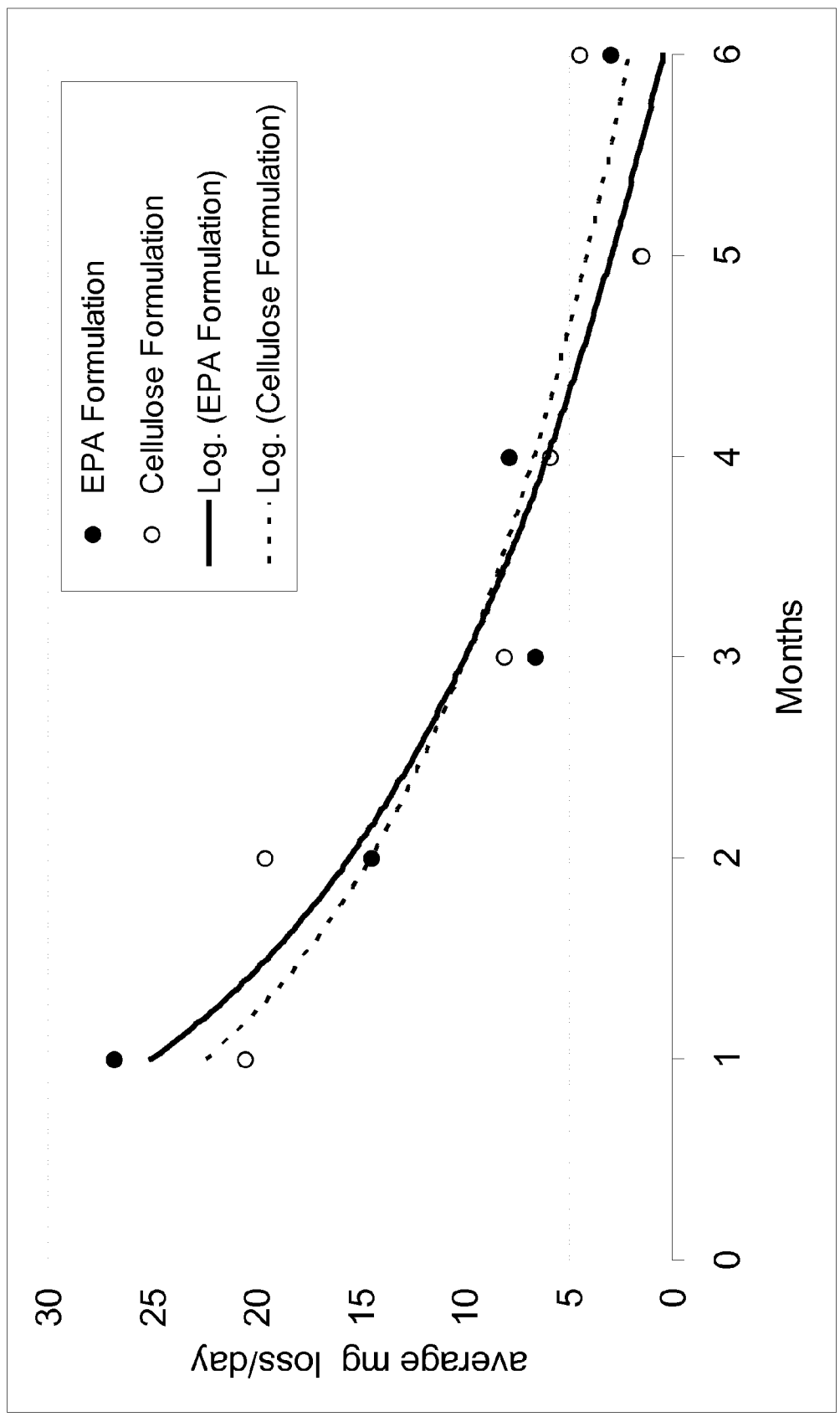
FIG. 2 provides results of active ingredient loss for ear tags tested as described in Example 11.
Figure 3:
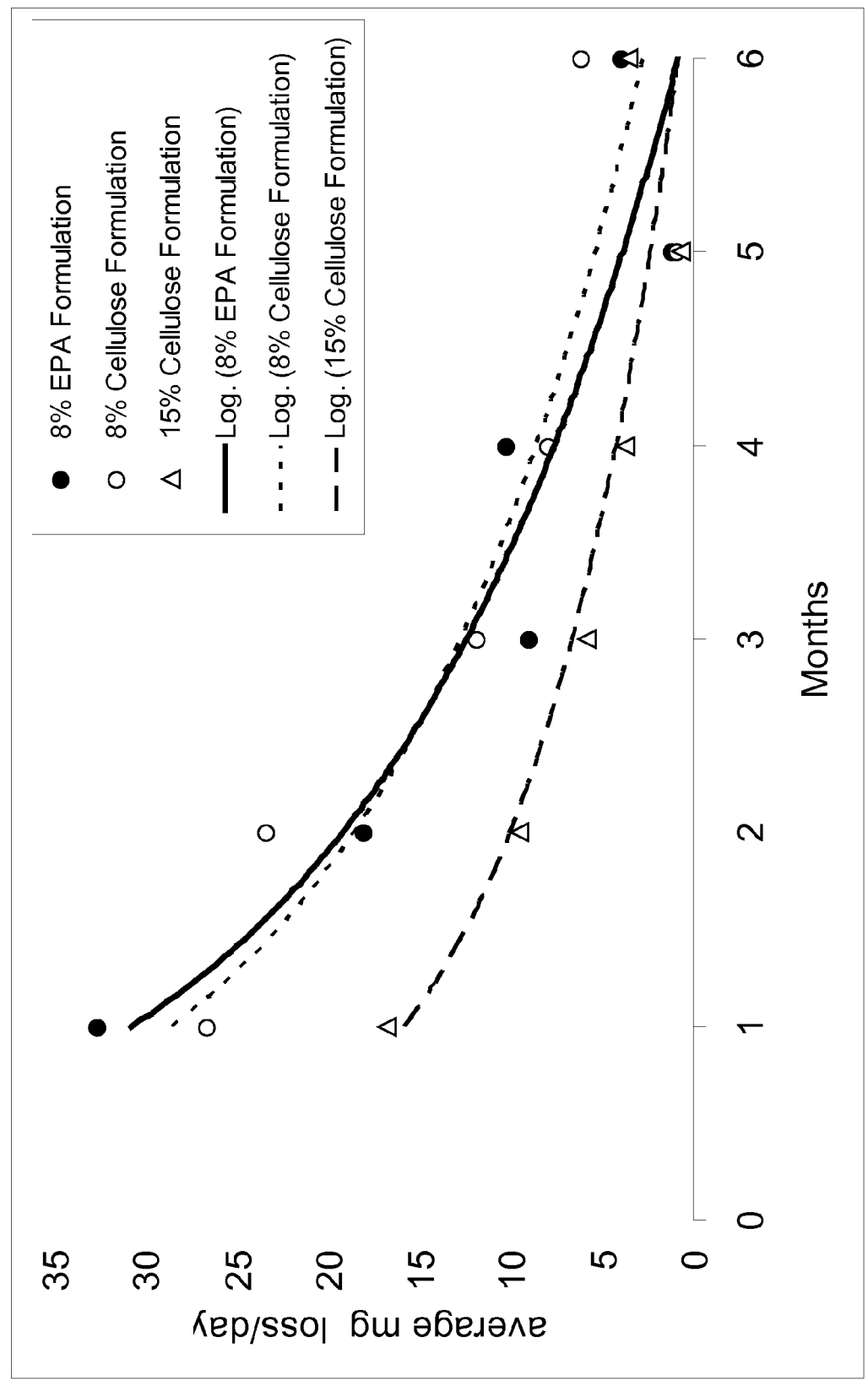
FIG. 3 provides results of active ingredient loss for ear tags tested as described in Example 11.

The results presented in Table 1 and in FIGS. 1, 2, and 3 indicate that there was no differences in the amount or rate of release of either beta-cyfluthrin or PBO from the EPA product when compared to the 8%+20% formulation containing the cellulose fibers.

The 15.0% beta-cyfluthrin formulation contained approximately 1.9 times as much beta-cyfluthrin as the other two formulations (15% versus 8%) and, with the exception of month 3, released at least 1.6 times as much beta-cyfluthrin during each month of the study and approximately 2.0 times as much beta-cyfluthrin over the entire 6 month study duration (Table 1 and FIG. 1).

The greater amount of beta-cyfluthrin released from the 15.0% beta-cyfluthrin formulation is expected to result in the improved efficacy of this formulation for control/repellency of face flies and horn flies when compared to the two 8% beta-cyfluthrin+20% PBO formulations.

Formula 10

| Ingredient | % w/w |
|---|---|
| Diazinon (85.98%) | 40.71 |
| Coumaphos (95.8%) | 15.66 |
| Cellulose Fibers | 12.00 |
| SuperKleen/2223 BF-95 (PVC/plasticizer blend, purchased from AlphaGary Co., Leominster, MA) | 30.53 |

TABLE 1

Active ingredient analysis and depletion rates of beta-cyfluthrin and PBO from ear tags removed from cattle at monthly intervals for six consecutive months.

8% beta-cyfluthrin + 20% PBO EPA Formulation

| Time point (months) | Date collected | Number days time point | Average wt of tag (mg) | Wt. PBO in tags (mg) | Wt. loss PBO from previous time point (mg) | Average wt loss of PBO mg/day/time point (mg) | Wt. beta cyfluthrin in tags (mg) | Wt. loss beta cyfluthrin from previous time point (mg) | Average wt loss beta cyfluthrin mg/day/time point (mg) | total active wt loss mg/day/time |
|---|---|---|---|---|---|---|---|---|---|---|
| 0 | Jun. 2, 2007 | 0 | 12906.1 | 2766 | 0 | | 1097 | 0 | | 0.0 |
| 1 | Jul. 2, 2007 | 30 | 12619.5 | 1963 | 803 | 26.8 | 888 | 209 | 7.0 | 33.7 |
| 2 | Aug. 1, 2007 | 30 | 11684.9 | 1532 | 431 | 14.4 | 760 | 128 | 4.3 | 18.6 |
| 3 | Aug. 31, 2007 | 30 | 11462.0 | 1337 | 195 | 6.5 | 686 | 74 | 2.5 | 9.0 |
| 4 | Oct. 3, 2007 | 33 | 10924.4 | 1079 | 258 | 7.8 | 607 | 79 | 2.4 | 10.2 |
| 5 | Nov. 7, 2007 | 35 | 10888.3 | 1027 | 52 | 1.5 | 622 | −15 | −0.4 | 1.1 |
| 6 | Dec. 8, 2007 | 31 | 10706.4 | 936 | 91 | 2.9 | 590 | 32 | 1.0 | 4.0 |

8% beta-cyfluthrin + 20% PBO Cellulose Formulation

| Time point (months) | Date collected | Number days time point | Average wt of tag (mg) | Wt. PBO in tags (mg) | Wt. loss PBO from previous time point (mg) | Average wt loss of PBO mg/day/time point (mg) | Wt. beta cyfluthrin in tags (mg) | Wt. loss beta cyfluthrin from previous time point (mg) | Average wt loss beta cyfluthrin mg/day/time point (mg) | total active wt loss mg/day/time |
|---|---|---|---|---|---|---|---|---|---|---|
| 0 | Jun. 2, 2007 | 0 | 14206.5 | 2842 | | | 1134 | 0 | | 0.0 |
| 1 | Jul. 2, 2007 | 30 | 13320.7 | 2227 | 615 | 20.5 | 922 | 212 | 7.1 | 26.6 |
| 2 | Aug. 1, 2007 | 30 | 12915.7 | 1641 | 586 | 19.5 | 782 | 140 | 4.7 | 24.2 |
| 3 | Aug. 31, 2007 | 30 | 11721.5 | 1400 | 241 | 8.0 | 667 | 115 | 3.8 | 11.9 |
| 4 | Oct. 3, 2007 | 33 | 11316.7 | 1209 | 191 | 5.8 | 599 | 68 | 2.1 | 7.8 |
| 5 | Nov. 7, 2007 | 35 | 11400.1 | 1159 | 50 | 1.4 | 617 | −18 | −0.5 | 0.9 |
| 6 | Dec. 8, 2007 | 31 | 11234.4 | 1024 | 135 | 4.4 | 565 | 52 | 1.7 | 6.1 |

15% beta-cyfluthrin Cellulose Formulation

| Time point (months) | Date collected | Number days time point | Average wt of tag (mg) | Wt. beta cyfluthrin in tags (mg) | Wt. loss beta cyfluthrin from previous time point (mg) | Average wt loss beta cyfluthrin mg/day/time point (mg) |
|---|---|---|---|---|---|---|
| 0 | Jun. 2, 2007 | 0 | 14467.5 | 1928 | 0 | |
| 1 | Jul. 2, 2007 | 30 | 13175.9 | 1445 | 483 | 16.1 |
| 2 | Aug. 1, 2007 | 30 | 12031.7 | 1173 | 272 | 9.1 |
| 3 | Aug. 31, 2007 | 30 | 10915.3 | 1100 | 73 | 2.4 |
| 4 | Oct. 3, 2007 | 33 | 10609.4 | 977 | 123 | 3.7 |
| 5 | Nov. 7, 2007 | 35 | 10416.8 | 951 | 26 | 0.7 |
| 6 | Dec. 8, 2007 | 31 | 10036.8 | 844 | 107 | 3.5 |

Example 12

This example evaluated the efficacy of two 35% diazinon plus 15% coumaphos insecticide cattle ear tag formulations (Formulas 10 and 11) for control of horn flies and face flies on cattle compared to the efficacy of a commercial standard 30% endosulfan ear tag (Avenger® Insecticide Cattle Ear Tags) (Formula 12).

-continued

| Ingredient | % w/w |
|---|---|
| D & C Green No. 6 (Color) | 0.10 |
| Titanium Dioxide | 1.00 |
| | 100.0% |

Formula 11

| Ingredient | % w/w |
|---|---|
| Diazinon (85.98%) | 40.71 |
| Coumaphos (95.8%) | 15.66 |
| PVC | 27.85 |
| Mark ® 1034 | 0.28 |
| Drapex ® 6.8 | 2.50 |
| Cellulose Fibers | 12.00 |
| Titanium Dioxide | 1.00 |
| | 100.0% |

Formula 12—Avenger Insecticide Cattle Ear Tags Containing 30% Endosulfan (EPA Reg. No. 61483-65).
Number of Test Animals per Treatment

| Formula | No. of animals |
|---|---|
| 10 | 26 |
| 11 | 40 |
| 12 | 25 |
| Untreated | 15 |

Horn fly and face fly counts were taken on ten randomly selected cows in each treatment group at each observation date. Counts were conducted on Day −1 prior to treatment and on Study Day 7 post-treatment and then weekly for the balance of the study. The study continued for 125 days (~18 weeks) post-treatment.

Horn Fly and Face Fly Efficacy: For both fly species, the following formula was used for determination of test results and for comparing efficacy of each treatment at each observation period.

$$\text{Percent of Flies} = 100 \times \frac{\text{Average No. of Flies on 10 Animals in Untreated Control Group} - \text{Average No. of Flies on 10 Animals in Treated Group}}{\text{Average No. of Flies on 10 Animals in Untreated Control Group}}$$

Figure 4:
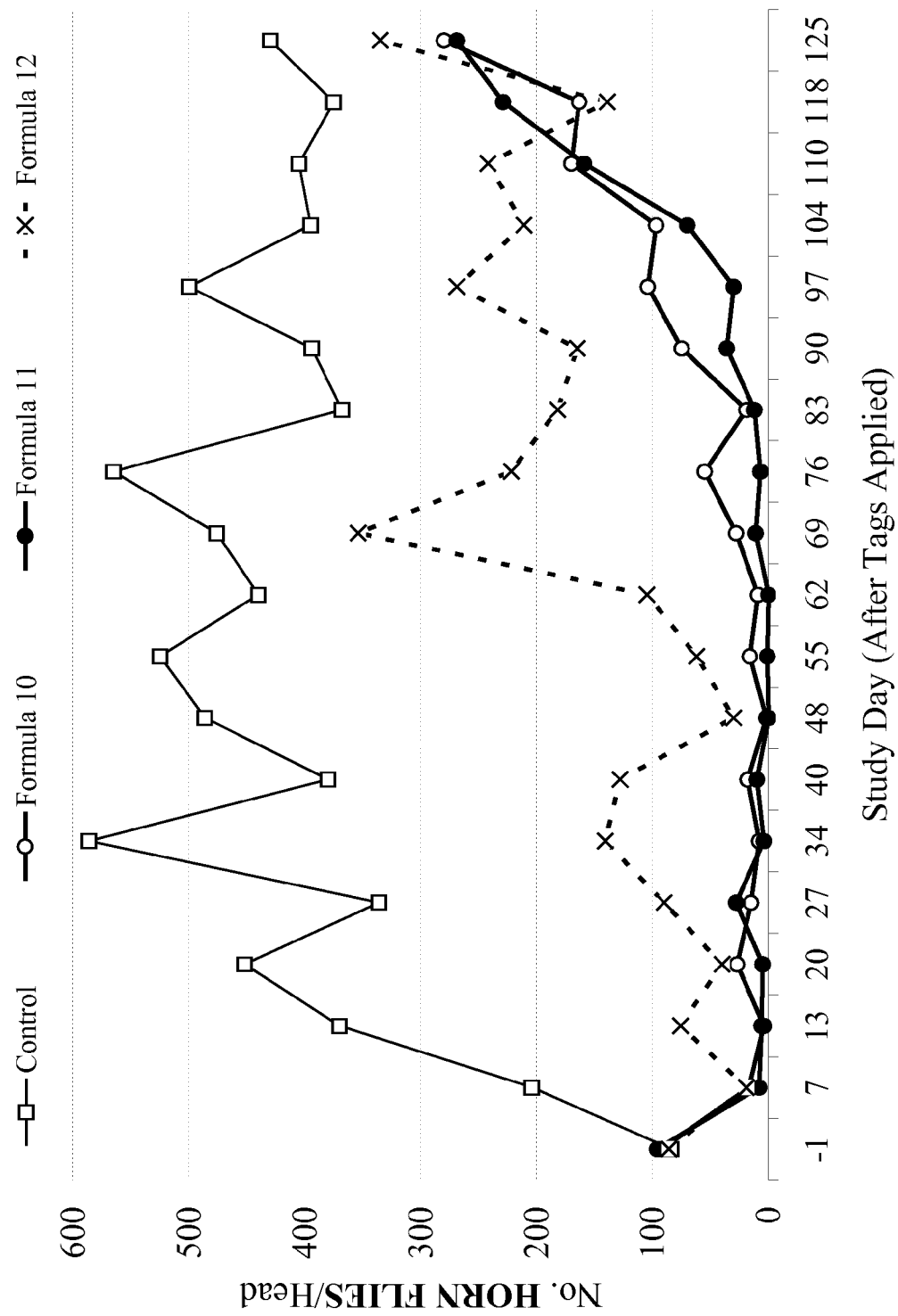
FIG. 4 provides horn fly count results for ear tags tested as descried in Example 12.
Figure 5:
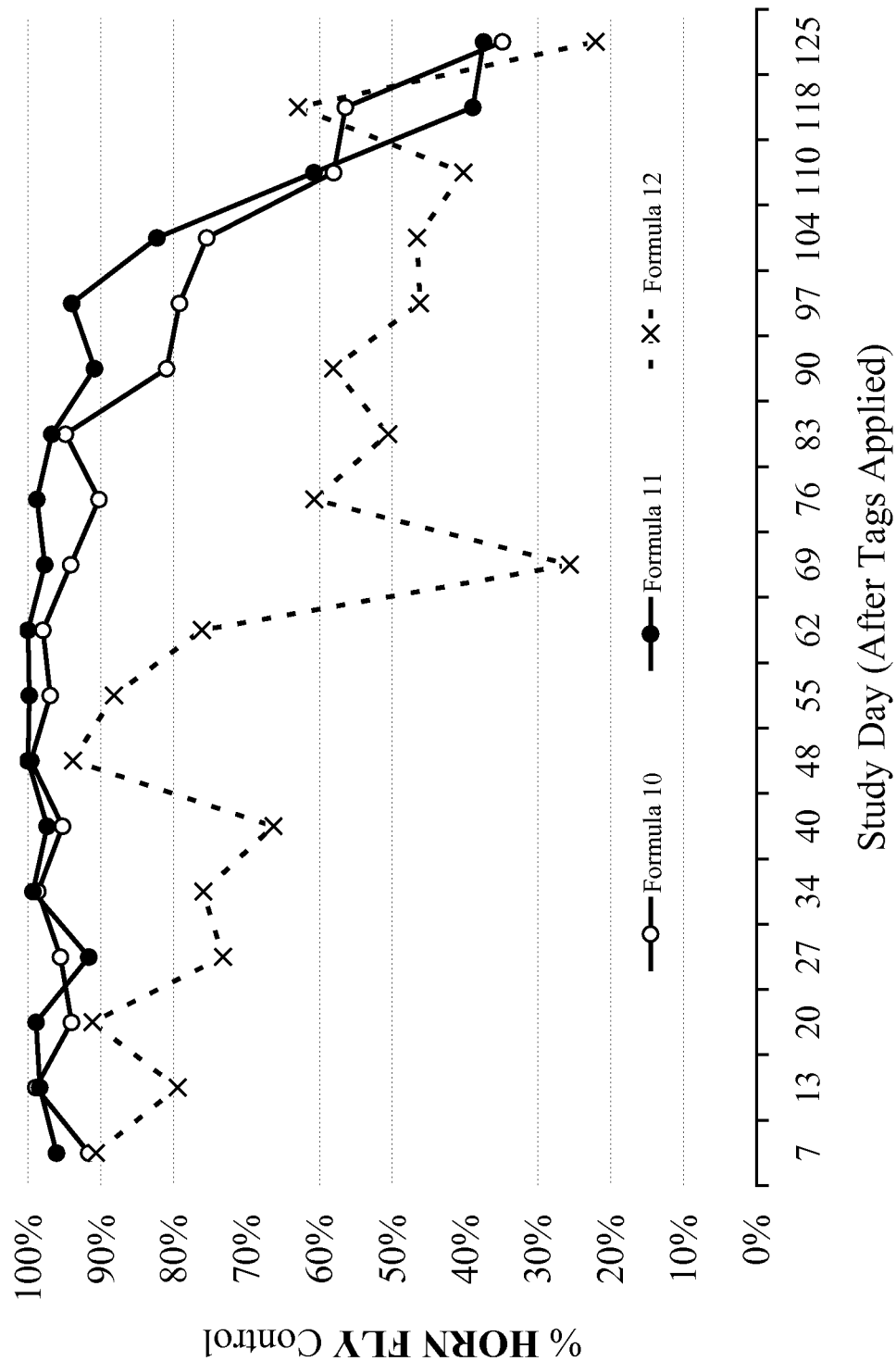
FIG. 5 provides horn fly count results for ear tags tested as descried in Example 12.

Efficacy of Treatments for Control of Horn Flies:
Pre- and post-treatment mean horn fly counts on cattle in each treatment group as compared to mean horn fly counts on the untreated control group are presented in Table 2 and illustrated in FIGS. 4 and 5.

TABLE 2

Average number (n = 10) of horn flies/animal for each treatment group and percent control as compared to the untreated control group.

| Treatment | Date (Study Day) Counts Conducted | | | | | | |
|---|---|---|---|---|---|---|---|
| Group-Treatment | 23 MAY 2008 (−1) | 31 MAY 2008 (7) | 06 JUN. 2008 (13) | 13 JUN. 2008 (20) | 20 JUN. 2008 (27) | 27 JUN. 2008 (34) | 03 JUL. 2008 (40) |
| Formula 10 | 92 | 17 | 4 | 27 | 15 | 8 | 18 |
| % Control | — | 92% | 99% | 94% | 96% | 99% | 95% |
| Formula 11 | 96 | 8 | 6 | 5 | 28 | 4 | 10 |
| % Control | — | 96% | 98% | 99% | 92% | 99% | 97% |
| Formula 12 | 86 | 19 | 76 | 40 | 105 | 141 | 128 |
| % Control | — | 91% | 79% | 91% | 69% | 76% | 66% |
| Untreated Control | 84 | 204 | 370 | 452 | 336 | 586 | 380 |

| Treatment | Date (Study Day) Counts Conducted | | | | | |
|---|---|---|---|---|---|---|
| Group-Treatment | 11 JUL. 2008 (48) | 18 JUL. 2008 (55) | 25 JUL. 2008 (62) | 01 AUG. 2008 (69) | 08 AUG. 2008 (76) | 15 AUG. 2008 (83) |
| Formula 10 | 2 | 16 | 9 | 28 | 55 | 19 |
| % Control | 99+% | 97% | 98% | 94% | 90% | 95% |
| Formula 11 | 0 | 1 | 0 | 11 | 7 | 12 |
| % Control | 100% | 99+% | 100% | 98% | 99% | 97% |
| Formula 12 | 30 | 62 | 105 | 354 | 222 | 182 |
| % Control | 94% | 88% | 76% | 26% | 61% | 51% |
| Untreated Control | 486 | 525 | 440 | 476 | 565 | 368 |

| Treatment | Date (Study Day) Counts Conducted | | | | | |
|---|---|---|---|---|---|---|
| Group-Treatment | 22 AUG. 2008 (90) | 29 AUG. 2008 (97) | 05 SEP. 2008 (104) | 11 SEP. 2008 (110) | 19 SEP. 2008 (118) | 26 SEP. 2008 (125) |
| Formula 10 | 75 | 104 | 97 | 170 | 163.4 | 280 |
| % Control | 81% | 79% | 75% | 58% | 56% | 35% |
| Formula 11 | 36 | 30 | 70 | 159 | 229 | 269 |
| % Control | 91% | 94% | 82% | 61% | 38% | 37% |
| Formula 12 | 165 | 269 | 211 | 242 | 139 | 335 |
| % Control | 58% | 46% | 46% | 40% | 62% | 22% |
| Untreated Control | 394 | 500 | 395 | 405 | 375 | 430 |

The Formula 10 tags provided >90% control of horn flies for 12 weeks (Day 83) post-treatment, and the Formula 11 tags provided >90% control of horn flies for 14 weeks (Day 97) post-treatment (Table 1 and FIG. 2).

Formula 12 [the commercial standard, Avenger (30% endosulfan] tags were less effective than the two diazinon/coumaphos tags (Formulas 10 and 11). The Formula 12 treatments only resulted in >90% control of horn flies on three observation dates post-treatment (Study Days 7, 20, and 48; Table 1, FIG. 2).

Figure 6:
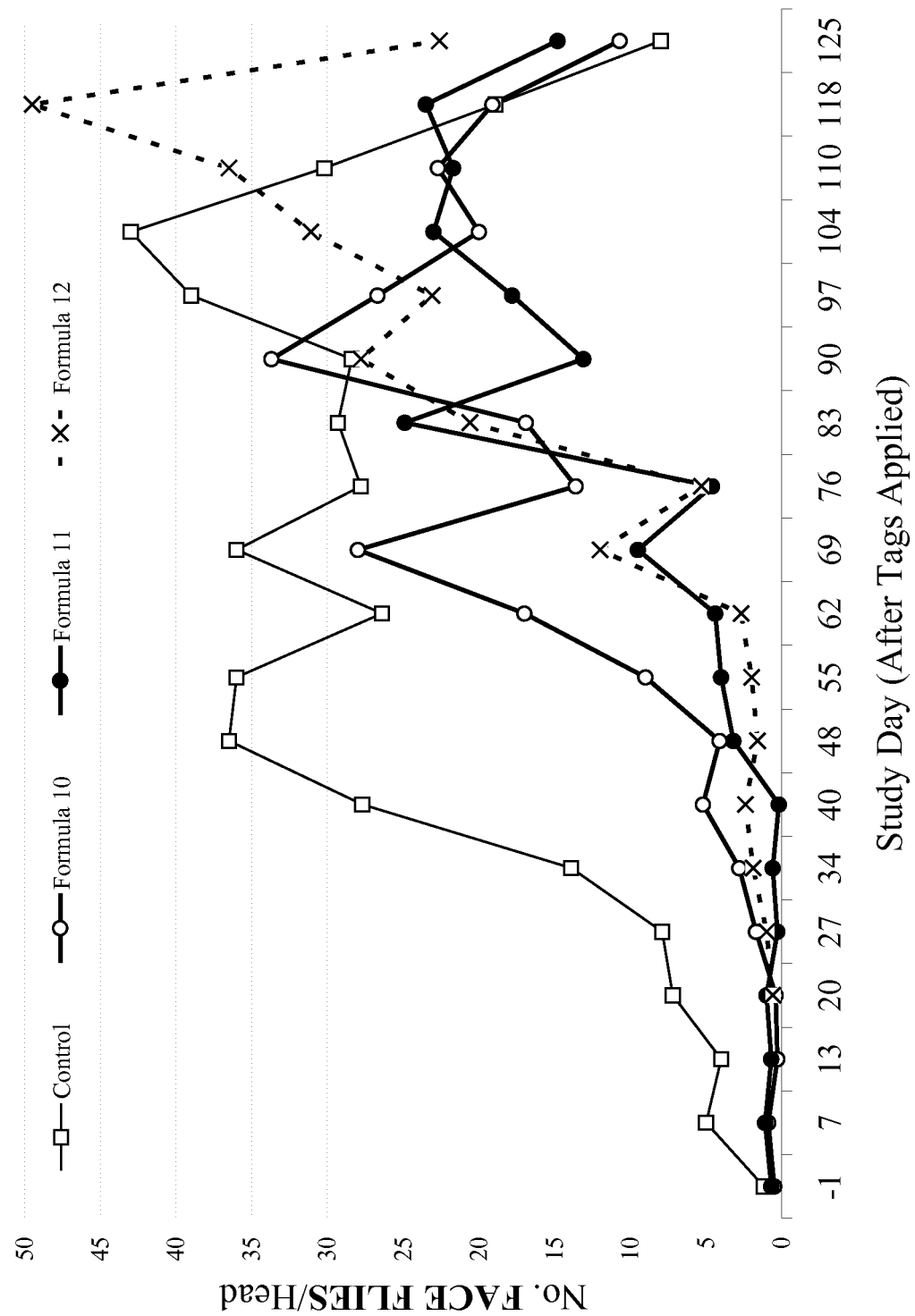
FIG. 6 provides results for pre- and post-treatment face fly counts for an untreated control group as described in Example 12.

Efficacy of Treatments for Control of Face Flies:

Pre- and post-treatment mean face fly counts on cattle in each treatment group as compared to mean face fly counts on the untreated control group are presented in Table 3 and illustrated in FIG. 6.

Figure 7:
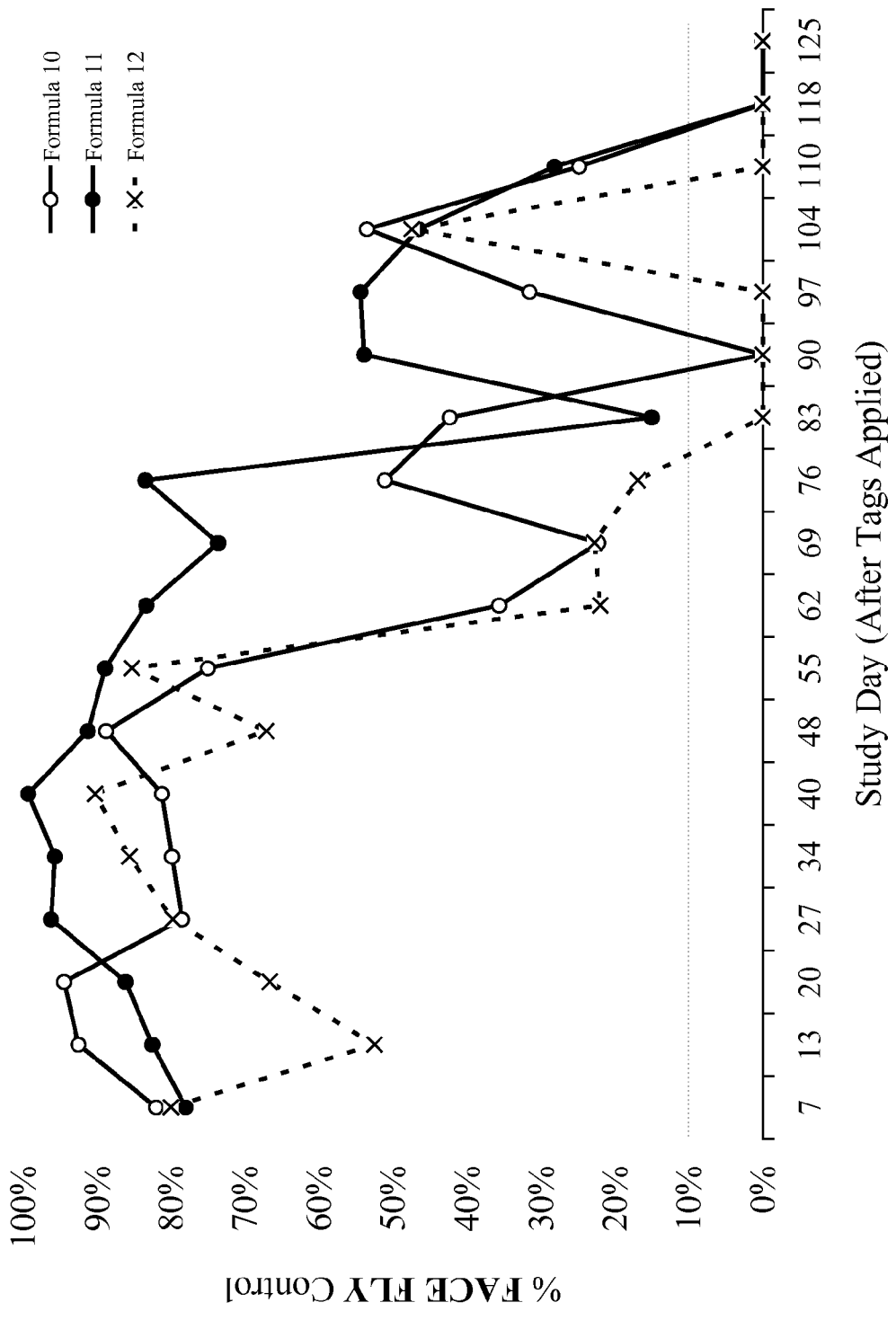
FIG. 7 provides results for pre- and post-treatment face fly counts for testing as described in Example 12.

The Formula 10 tags provided >75% control of face flies for 8 weeks (Day 55) post-treatment, and Formula 11 tags provided >74% control of face flies for 11 weeks (Day 76) post-treatment (Table 3, FIG. 7).

Example 13—Diazinon, Cellulose, and Silicon Dioxide

| % w/w | Ingredients |
|---|---|
| 34.0 | 1. Diazinon (88%) |
| 14.0 | 2. Cab-O-Sil |
| 40.0 | 3. SuperKleen 2223BF-95 (PVC/plasticizer blend, purchased from AlphaGary Co., Leominster, MA) |
| 12.0 | 4. Cellulose Fibers |
| 100.0% | |

Mixed Ingredients 2 and 3 in a Marion mixer with Paddle blender and set aside. Add 1 to 4 and then added mix of 2 and 3 and heated to 170° F. and mixed for 3 hours. Injection molded using Trubor 50 ton/3.5 oz injection molder.

TABLE 3

Average number (n = 10) of face flies/head for each treatment group and percent control as compared to theu ntreated control group.

| Treatment | Date (Study Day) Counts Conducted | | | | | | |
|---|---|---|---|---|---|---|---|
| Group-Treatment | 23 MAY 2008 (−1) | 31 MAY 2008 (7) | 06 JUN. 2008 (13) | 13 JUN. 2008 (20) | 20 JUN. 2008 (27) | 27 JUN. 2008 (34) | 03 JUL. 2008 (40) |
| Formula 10 | 0.5 | 0.9 | 0.3 | 0.4 | 1.7 | 2.8 | 5.2 |
| % Control | — | 82% | 93% | 94% | 78% | 80% | 81% |
| Formula 11 | 0.7 | 1.1 | 0.7 | 1.0 | 0.3 | 0.6 | 0.2 |
| % Control | — | 78% | 83% | 86% | 96% | 96% | 99% |
| Formula 12 | 0.6 | 1.0 | 1.9 | 2.4 | 1.6 | 2.0 | 2.7 |
| % Control | — | 80% | 53% | 67% | 80% | 86% | 90% |
| Untreated Control | 1.2 | 5.0 | 4.0 | 7.2 | 7.9 | 13.9 | 27.7 |

| Treatment | Date (Study Day) Counts Conducted | | | | | |
|---|---|---|---|---|---|---|
| Group-Treatment | 11 JUL. 2008 (48) | 18 JUL. 2008 (55) | 25 JUL. 2008 (62) | 01 AUG. 2008 (69) | 08 AUG. 2008 (76) | 15 AUG. 2008 (83) |
| Formula 10 | 4.1 | 9.0 | 17.0 | 28.0 | 13.6 | 16.9 |
| % Control | 89% | 75% | 36% | 22% | 51% | 42% |
| Formula 11 | 3.2 | 4.0 | 4.4 | 9.5 | 4.6 | 24.9 |
| % Control | 91% | 89% | 83% | 74% | 83% | 15% |
| Formula 12 | 12.0 | 5.3 | 20.6 | 27.8 | 23.1 | 31.1 |
| % Control | 67% | 85% | 22% | 23% | 17% | 0% |
| Untreated Control | 36.5 | 36.0 | 26.4 | 36.0 | 27.8 | 29.3 |

| Treatment | Date (Study Day) Counts Conducted | | | | | |
|---|---|---|---|---|---|---|
| Group-Treatment | 22 AUG. 2008 (90) | 29 AUG. 2008 (97) | 05 SEP. 2008 (104) | 11 SEP. 2008 (110) | 19 SEP. 2008 (118) | 26 SEP. 2008 (125) |
| Formula 10 | 33.7 | 26.7 | 20.0 | 22.7 | 19.1 | 10.7 |
| % Control | 0% | 31% | 53% | 25% | 0% | 0% |
| Formula 11 | 13.1 | 17.8 | 23.0 | 21.7 | 23.5 | 14.3 |
| % Control | 54% | 54% | 46% | 28% | 0% | 0% |
| Formula 12 | 36.5 | 49.5 | 22.6 | 44.8 | 18.9 | 17.9 |
| % Control | 0% | 0% | 47% | 0% | 0% | 0% |
| Untreated Control | 28.4 | 39.0 | 43.0 | 30.2 | 18.9 | 8.0 |

Face fly control provided by Formula 12 [the commercial standard Avenger tags (30% endosulfan)] was erratic for the first 8 weeks post-treatment, ranging from 53 to 90% control, and diminished rapidly after Day 55 (Table 3, FIG. 7).

In this study, both 35% diazinon+15% coumaphos ear tag formulations were clearly more efficacious for control of horn flies and face flies than the commercial standard Avenger tags.

Put 10 tags in clay coated laminated foil pouches at ambient temperature and 1 tag in a glass jar at ambient temperature and 1 tag in a glass jar at 50° C. After 72 hours in 50° C. oven, tag was slightly wet (minor bleeding at the bottom of the jar). After sitting at ambient temperature, the packaged and unpackaged tags looked good (dry).

Example 14—Diazinon, Coumaphos, Cellulose, and Silicon Dioxide

| % w/w | Ingredients |
|---|---|
| 45.5 | 1. Diazinon (88%) |
| 10.4 | 2. Coumaphos (95.8) |
| 3.0 | 3. Cab-O-Sil |
| 29.1 | 4. SuperKleen 2223BF-95 (PVC/plasticizer blend, purchased from AlphaGary Co., Leominster, MA) |
| 12.0 | 5. Cellulose Fibers |
| 100.0% | |

Mixed Ingredients 1, and 3 in a Marion mixer with Paddle blender and set aside. Mixed 4 and 5 until homogenous and added mixture of 1 and 3. The blend was not heated. Added ingredient 2 and mixed for 1 hour. Injection molded using Trubor 50 ton/3.5 oz injection molder.

Put 10 tags in clay coated laminated foil pouches at ambient temperature and 1 tag in a glass jar at ambient temperature and 1 tag in a glass jar at 50° C. After 72 hours in 50° C. oven, tag was wet (pooling at the bottom of the jar). After sitting at ambient temperature, the packaged and unpackaged tags looked good (dry). Placed an ambient tag that was dry after 72 hours in 50° C. oven and after 24 hours the tag was wet.

The invention claimed is:

1. A method of making a pesticidal ear tag comprising:
   a. mixing a polymer and cellulose fibers derived from wood pulp to form a polymer mixture;
   b. heating the polymer mixture;
   c. adding a pesticidal active ingredient to the polymer mixture;
   d. cooling the polymer mixture; and
   e. injection molding the polymer mixture to form the ear tag,
   wherein the cellulose fibers comprise from about 2% to about 20% by weight of the total weight of the ear tag.

2. The method of claim 1 wherein the polymer is selected from the group consisting of polyvinyl chloride, polyolefin, polyurethane, polyamide, methacrylate, silicon polymers, polyvinyl halides, polyacrylate esters, polymethacrylate esters, polymers of vinyl benzene, and combinations thereof.

3. The method of claim 2 wherein the polymer is polyvinyl chloride.

4. The method of claim 1 wherein the polymer comprises from about 20% to about 60% of the total weight of the ear tag.

5. The method of claim 1 wherein the pesticidal active ingredient is in liquid form or dissolved in solvent.

6. The method of claim 5 wherein the pesticidal active ingredient is in liquid form.

7. The method of claim 1 wherein the pesticidal active ingredient is selected from the group consisting of organophosphate, pyrethroid, carbamate, nicotinoid, organochlorine, pyrrole, pyrazole, oxadiazine, macrocyclic lactone, and combinations thereof.

8. The method of claim 7 wherein the pesticidal active ingredient is an organophosphate and wherein the organophosphate is diazinon.

9. The method of claim 8 wherein the pesticidal active ingredient further comprises coumaphos.

10. The method of claim 7 wherein the pesticidal active ingredient is a pyrethroid and wherein the pyrethroid is beta-cyfluthrin.

11. The method of claim 7 wherein the pesticidal active ingredient comprises from about 10% to about 70% by weight of the total weight of the ear tag.

12. The method of claim 9 wherein a mixture of diazinon and coumpahos is present in an amount from about 40% to about 60% by weight of the total weight of the ear tag, cellulose fiber is present in an amount from about 5% to about 15% by weight of the total weight of the ear tag, and the polymer is present in an amount of from about 35% to about 45% by weight of the total weight of the ear tag.

13. The method of claim 10 wherein beta-cyfluthrin is present in an amount from about 40% to about 60% by weight of the total weight of the ear tag, cellulose fiber is present in an amount from about 5% to about 15% by weight of the total weight of the ear tag, and the polymer is present in an amount of from about 35% to about 45% by weight of the total weight of the ear tag.

14. The method of claim 1 wherein the cellulose fibers are selected from the group consisting of softwood fibers and hardwood fibers.

15. The method of claim 14 wherein:
   the softwood fibers are derived from slash pine, jack pine, radiata pine, loblolly pine, white spruce, lodgepole pine, redwood, or douglas fir; and
   the hardwood fibers are derived from oak, genus *Quercus*, maple, genus *Acer*, poplar, or genus *Populus*.

16. The method of claim 14 wherein the cellulose fibers are prepared by a Kraft process or a sulfite process.

17. The method of claim 16 wherein the cellulose fibers are selected from the group consisting of Southern Softwood Kraft, Northern Softwood Kraft, hardwood, eucalyptus, mechanical, recycle, rayon, and combinations thereof.

18. The method of claim 17 wherein the cellulose fibers are Southern Softwood Kraft.

19. The method of claim 1 further comprising mixing a plasticizer and a stabilizer with the polymer mixture after cooling the mixture but prior to injection molding, wherein:
   the plasticizer is selected from the group consisting of phthalates, sebacates, adipates, citrates, trimellitates, hydrogenated polyphenols, alkylated aromatic hydrocarbons, polyester plasticizers, polycarboxylic acids, epoxide plasticizers, esters of azelaic acid, esters of maleic acid, esters of ricinolic acid, esters of myristic acid, esters of palmitic acid, esters of oleic acid, esters of stearic acid, esters of trimelletic acid, and mixtures thereof; and
   the stabilizer is selected from the group consisting of anti-oxidants, ultraviolet stabilizers, and polymer stabilizers.

20. An ear tag made by a method according to claim 1.

* * * * *